United States Patent
Newbold et al.

(10) Patent No.: US 9,322,749 B2
(45) Date of Patent: Apr. 26, 2016

(54) AUTOMATIC SAMPLING SYSTEM FOR SAMPLING FROM ENCLOSED CONTAINERS

(71) Applicant: Bend Research, Inc., Bend, OR (US)

(72) Inventors: David Dixon Newbold, Bend, OR (US); Douglas Lee Millard, Bend, OR (US); George Lewis Ellis, Jr., LaPine, OR (US)

(73) Assignee: Bend Research, Inc., Bend, OR (US)

(*) Notice: Subject to any disclaimer, the term of this patent is extended or adjusted under 35 U.S.C. 154(b) by 249 days.

(21) Appl. No.: 14/072,263

(22) Filed: Nov. 5, 2013

(65) Prior Publication Data

US 2014/0123777 A1    May 8, 2014

Related U.S. Application Data

(60) Provisional application No. 61/722,742, filed on Nov. 5, 2012.

(51) Int. Cl.
*G01N 1/14* (2006.01)
*C12M 1/26* (2006.01)
*G01N 1/10* (2006.01)

(52) U.S. Cl.
CPC ............ *G01N 1/14* (2013.01); *C12M 33/04* (2013.01); *G01N 2001/1037* (2013.01)

(58) Field of Classification Search
CPC ........... G01N 1/14; G01N 2001/1418; G01N 2001/1427
USPC ............... 73/863.71–863.73, 863.83–863.96, 73/863.74, 863.81, 864.63, 864.74, 73/864.81; 137/240–241
See application file for complete search history.

(56) References Cited

U.S. PATENT DOCUMENTS

| | | | |
|---|---|---|---|
| 3,379,216 A | 4/1968 | Mercier | |
| 3,713,988 A | 1/1973 | Dawson et al. | |
| 3,771,562 A | 11/1973 | Curran | |
| 3,807,906 A | 4/1974 | Breit | |
| 4,347,877 A | 9/1982 | Hoiss | |
| 4,548,088 A * | 10/1985 | Hood, Jr. ................. | 73/864.34 |
| 4,889,812 A | 12/1989 | Guinn et al. | |
| 4,918,019 A | 4/1990 | Guinn | |
| 5,296,197 A | 3/1994 | Newberg et al. | |
| 5,630,935 A | 5/1997 | Treu | |
| 6,085,602 A | 7/2000 | Schorn et al. | |
| 6,133,022 A | 10/2000 | Newberg | |

(Continued)

FOREIGN PATENT DOCUMENTS

| FR | 2617286 | 12/1988 |
|---|---|---|
| WO | WO 2006/086489 | 8/2006 |
| WO | WO 2011/038008 | 3/2011 |

OTHER PUBLICATIONS

Benz. "Bioreactor Designs for Chemical Engeneers" Chem. Eng. Progress 107.8 (2011): 21-26.

(Continued)

*Primary Examiner* — Peter Macchiarolo
*Assistant Examiner* — Anthony W Megna Fuentes
(74) *Attorney, Agent, or Firm* — Klarquist Sparkman, LLP

(57) ABSTRACT

A sample can be collected from an enclosed container by opening a sample collection valve and drawing the sample from the enclosed container. After delivery of the sample out of a fluid flow path, a sanitizing fluid can be directed along the fluid flow path to sanitize the fluid flow path.

17 Claims, 6 Drawing Sheets

(56) References Cited

U.S. PATENT DOCUMENTS

| | | |
|---|---|---|
| 6,423,548 B1 | 7/2002 | Newberg et al. |
| 6,491,283 B2 | 12/2002 | Newberg |
| 6,821,773 B1 | 11/2004 | Newberg |
| 7,192,003 B2 | 3/2007 | Hoobyar et al. |
| 7,389,792 B2 | 6/2008 | Newberg |
| 2002/0036017 A1 | 3/2002 | Leys et al. |
| 2007/0039653 A1 | 2/2007 | Maggard |
| 2007/0128087 A1 | 6/2007 | Cannizzaro et al. |
| 2007/0131289 A1 | 6/2007 | Pataki |
| 2008/0032380 A1 | 2/2008 | Kleis et al. |
| 2009/0038419 A1 | 2/2009 | Hiller et al. |
| 2009/0178495 A1 | 7/2009 | Steigmiller et al. |
| 2009/0199904 A1 | 8/2009 | Babbitt et al. |
| 2010/0043883 A1 | 2/2010 | Yu et al. |
| 2010/0047122 A1 | 2/2010 | Barringer, Jr. |
| 2010/0102008 A1 | 4/2010 | Hedberg |
| 2010/0236340 A1 | 9/2010 | Lee et al. |

OTHER PUBLICATIONS

Daken Stainless Products: "Keofitt W15 Sample Valves", (Jan. 1, 2005), Available at http://www.keofitt-uk.com/865541.htm [last accessed on Jul. 6, 2012].

* cited by examiner

AUTOMATIC SAMPLING SYSTEM FOR SAMPLING FROM ENCLOSED CONTAINERS

CROSS-REFERENCE TO RELATED APPLICATION

This application claims the benefit of U.S. Provisional Application No. 61/722,742, which was filed on Nov. 5, 2012 and is incorporated herein by reference in its entirety.

FIELD

The present disclosure is directed to an automatic aseptic sampling valve and methods of using the same.

BACKGROUND

Obtaining samples from containers or other systems that support biologically and/or chemically active environments can require complex and careful sampling procedures to avoid contamination of the containers or the environment itself. For example, most bioreactors require frequent sampling (e.g., one or more times a day) to monitor and control the conditions and levels of nutrients needed for cell growth. To reduce the risk of contamination within such systems, conventional sampling techniques generally require operators to perform multiple, labor-intensive steps.

SUMMARY

In some embodiments, the sampling systems and methods disclosed herein provide consistent sampling procedures for obtaining samples of a desired quality, while reducing the risk of contamination of the enclosed container and the need for labor-intensive operator attention.

In one embodiment, a sampling system for collecting a fluid sample from an enclosed container is provided. The system comprises (a) a sampling module having a sample collection valve operable between an open position and a closed position, a chamber, and a moveable member within the chamber; (b) a first outlet valve operable between a waste delivery position and a non-waste delivery position; (c) a fluid flow path interconnecting the sample collection valve and first outlet valve; (d) a sanitizing fluid valve; and (e) a purging gas valve. The sampling module can withdraw a sample from the enclosed container into the chamber when the sample collection valve is in the open position, and the moveable member can discharge the sample from the chamber and into the fluid flow path of the sampling system for subsequent analysis when the sample collection valve is in the closed position.

In some embodiments, the sampling module comprises a syringe pump and the moveable member comprises a piston member within a chamber of the sampling module. The system can also include a pump member that is operatively coupled to the sampling module to cause the moveable member to move within the chamber to discharge fluid from within the chamber.

In some embodiments, after discharge of the sample for subsequent analysis and with the first outlet valve in the non-waste delivery position, a sanitizing fluid can be introduced into the fluid flow path via the sanitizing fluid inlet to sanitize the apparatus along the fluid flow path. After sanitizing the apparatus, the first outlet valve can be moved to the waste delivery position and a gas can be introduced into the fluid flow path and discharged out the first outlet valve.

The sanitizing fluid inlet can be at an upstream portion of the fluid flow path and the first outlet valve can be at a downstream portion of the fluid flow path. The sanitizing fluid can flow through the fluid flow path from between the sanitizing fluid inlet to the first outlet valve to sanitize the fluid flow path therebetween.

In some embodiments, the non-waste delivery position of the first outlet valve comprises a first orientation wherein the sample in the fluid flow path can pass through the first outlet valve for subsequent analysis and a second orientation wherein no fluid can pass through the first outlet valve. The sanitizing fluid inlet and gas inlet can both be positioned upstream of the sample collection valve.

In another embodiment, a method of collecting a fluid sample from an enclosed container is provided. The method can include positioning a sampling module within a dip tube port of the enclosed chamber; opening a sample collection valve in the sampling module and drawing a fluid sample from the enclosed container into a chamber of the sampling module; directing the fluid sample out of the chamber along the fluid flow path; discharging the fluid sample out of the fluid flow path for subsequent analysis; closing a waste valve and directing sanitizing fluid through a sanitizing fluid inlet along the fluid flow path past the closed sampling valve to sanitize the fluid flow path; and discharging the sanitizing fluid out of the fluid flow path.

In some embodiments, after discharging the sanitizing fluid but before drawing another fluid sample, the method also includes opening the waste valve and directing a gas through a gas inlet and along the fluid flow path and discharging the gas through the open waste valve to purge the sanitizing fluid from the fluid flow path. In other embodiments, the act of directing the fluid sample out of the chamber along the fluid flow path can include causing a piston to move towards the fluid sample to force the fluid sample out of the chamber.

The foregoing and other objects, features, and advantages of the invention will become more apparent from the following detailed description, which proceeds with reference to the accompanying figures.

DETAILED DESCRIPTION

Figure 1:
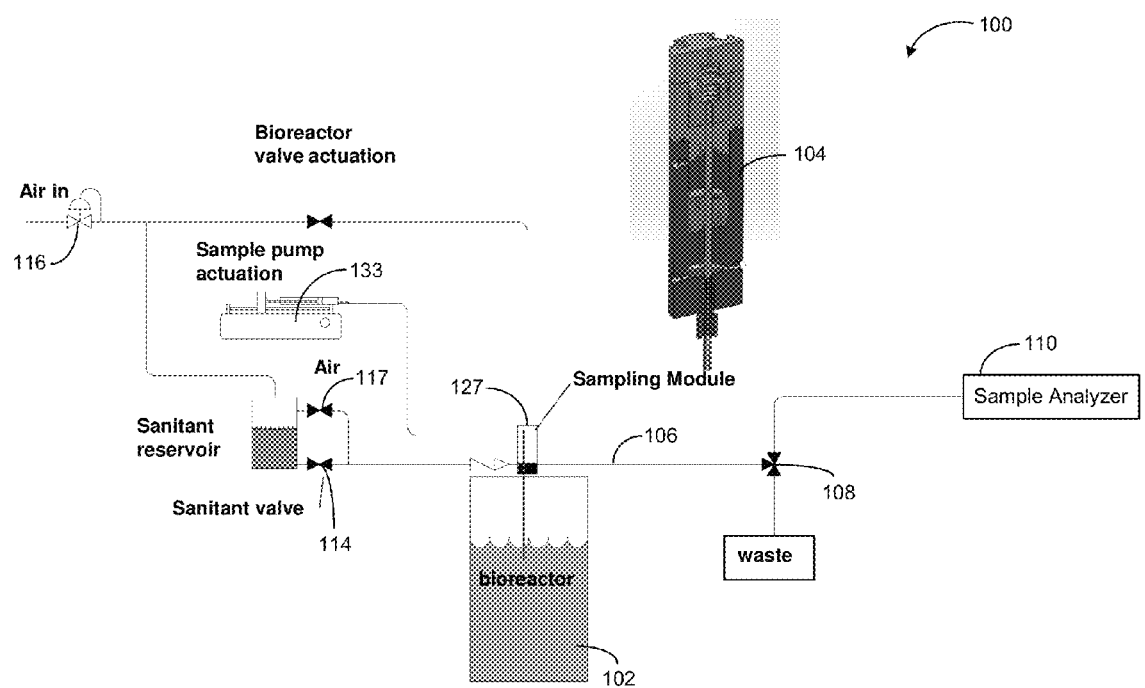
FIG. 1 illustrates a schematic view of a sampling system for obtaining samples from enclosed containers.

Various embodiments of sampling systems and their methods of use are disclosed herein. The following description is exemplary in nature and is not intended to limit the scope, applicability, or configuration of the invention in any way. Various changes to the described embodiment may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

The terms "upstream" and "downstream" are not absolute terms; instead, those terms refer to the direction of flow of fluids within a channel or pathway. Thus, with regard to a structure through which a fluid flows, a first area is "upstream" of a second area if the fluid flows from the first area to the second area. Likewise, the second area can be considered "downstream" of the first area.

Unless otherwise indicated, all numbers expressing quantities of ingredients, properties such as molecular weight, percentages, measurements, distances, ratios, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Enclosed containers, such as bioreactors can require sampling one or more times during a day to monitor cell growth. Conventional sampling techniques are generally labor intensive and require multiple steps. If sampling is to be performed multiple times within a day, operators are generally required to be available during those times to perform the conventional labor-intensive steps in conventional sampling processes.

The systems and methods described herein provide improved sampling techniques for obtaining samples from enclosed containers. Although these systems and methods can be manually operated, in some embodiments the operation of these systems and methods can be automated to reduce the amount of operator supervision required during operation.

FIG. 1 illustrates a sampling system 100 for obtaining a sample from an enclosed container 102 or other similar containers or systems that support biologically and/or chemically active environments. Sampling system 100 includes a sampling module 104 that can receive a sample and deliver the sample along a fluid flow path 106 to another location. For example, as shown in FIG. 1, the sample can be delivered along the flow path 106 to an outlet valve 108. Outlet valve 108 can open or close to allow or restrict, respectively, the flow of samples through outlet valve 108. After the sample exits outlet valve 108, the sample can be directed into another location, such as a sample/analyzer 110 for analysis, processing, and/or delivery to another system for analysis and/or processing. In one embodiment, the sample/analyzer 110 can comprise an automated analyzer, such as a bioprofile analyzer available from Nova Biomedical of Waltham, Mass.

The samples that are dispensed from outlet valve 108 for analysis or processing are desirably representative of the materials in the enclosed container 102 at the time the sample was taken. To reduce the risk of contamination, dilution, or alteration of the composition of the samples taken from sample collection valve 104 and delivered through flow path 106, a sanitizing fluid can be delivered through a portion of flow path 106 that comes into contact with the samples.

To introduce the sanitizing fluid into flow path 106, a sanitizing fluid inlet valve 114 is provided upstream of sampling module 104. Sanitizing fluid inlet valve 114 is operable between a closed position that restricts fluid flow through sanitizing fluid inlet valve 114 and an open position that allows fluid flow through sanitizing fluid inlet valve 114. In some embodiments, some or all of the valves can be biased closed.

In one embodiment, the sanitizing fluid is any fluid that can sanitize, disinfect, or sterilize the valve. The sanitizing fluid can be a liquid, a gas, or a combination thereof. Sanitizing fluids include steam, ethylene oxide, glutaraldehyde, formaldehyde, formalin, chlorine gas, hypochlorite, bromine, hypobromite, iodine, hypoiodite, bromine chloride, chlorine dioxide, ozone, hydrogen peroxide, monochloramine, dichloramine, trichloramine, quatinary ammonium salts, ethanol, 70% ethanol/water, isopropanol, 70% isopropanol/water, peroxyacetic acid, and peracetic acid. In one embodiment, the sanitizing fluid is steam. In another embodiment, the sanitizing fluid is ethylene oxide. In another embodiment, the sanitizing fluid is glutaraldehyde.

A gas inlet valve 116 can also be provided upstream of sampling module 104 to deliver a gas through flow path 106. The gas can eliminate and/or reduce the amount of sanitizing fluid remaining within flow path 106 after flow path 106 is exposed to the sanitizing fluid. The sanitizing fluid can clean the path and/or remove any material from previous samples in the area contacted by the sanitizing fluid. Gas inlet valve 116 is operable between a closed position that restricts the flow of gas through gas inlet valve 116 and an open position that allows the flow of gas through gas inlet valve 116. In one embodiment, the gas comprises compressed air.

As shown in FIG. 1, at least some portion of the gas path overlaps with the sanitant path, which in turn overlaps at least in part with flow path 106, to permit the gas to purge the sanitant from flow path 106. For example, as shown in FIG. 1, a second gas inlet valve 117 can be provided in the vicinity of sanitizing fluid inlet valve 114.

Figure 2A:
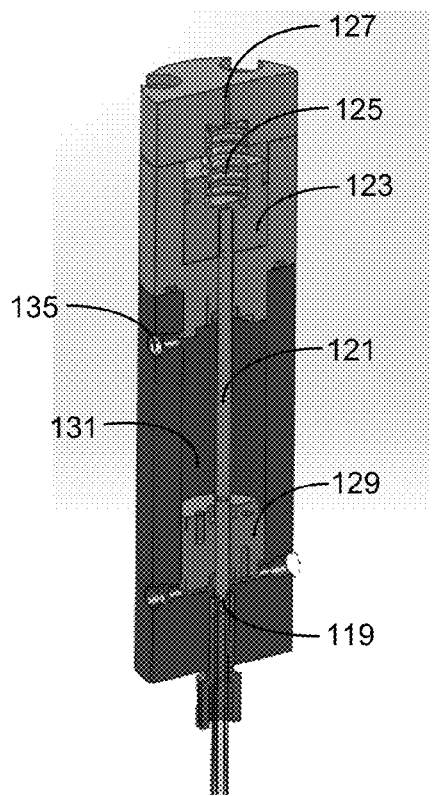
FIGS. 2A-2B illustrate schematic views of the sampling module shown in FIG. 1.
Figure 2B:
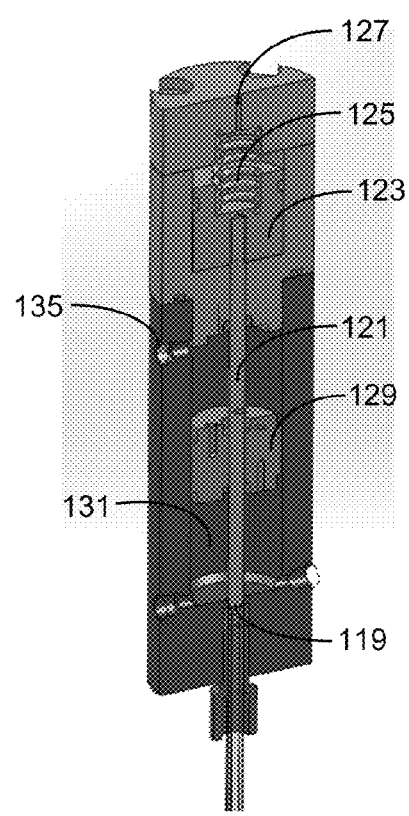

FIGS. 2A and 2B illustrate additional details of an exemplary sampling module 104. In this embodiment, sampling module 104 can comprise a syringe pump and valve integrated system. In one embodiment, sampling module 104 can comprise a relatively compact cylinder that can be mounted directly on a dip tube port of an enclosed container 102. As described in more detail below, the system can take samples from an enclosed container 102 (e.g., whole broth samples) by drawing a sample into the pump and then pushing the sample at positive pressure to a desired delivery location (e.g., sample/analyzer 110).

Sampling module 104 can have a sample collection valve 119 that can move between a closed and open position. When sample collection valve 119 is in the open position, a sample can be drawn from the enclosed container 102 into sampling module 104. Sample collection valve 119 can comprise a valve stem 121 coupled to a first piston 123. First piston 123 can be coupled to a bias member (e.g., by spring member 125) so that sample collection valve 119 is biased towards the closed position. When first piston 123 is moved upwards, valve stem 121 also moves upwards and opens sample collection valve 119.

In the exemplary embodiment, air-operated valves can utilize air pressure to move first piston 123 as desired to open or close sample collection valve 119. For example, as shown in FIG. 1, a gas inlet valve 116 can be coupled to air source and the upward movement of first piston 123 results in sample collection valve 119 opening.

Although the operation of first piston 123 (and, in turn sample collection valve 119) is described herein as controlled by pneumatic operation, it should be understood that other control mechanisms that are capable of moving first piston 123 in the manner described are possible.

Referring again to FIGS. 2A and 2B, a second piston 129 can be provided that is movable within a chamber 131 of sampling module 104. Second piston 129 can be configured to move freely within chamber 131. When sample collection valve 119 opens, second piston 129 can move upward to allow sample to be drawn into chamber 131. To discharge sample (or sanitizing fluid) from chamber 131, second piston can be forced to move downward thereby forcing the sample (or sanitizing fluid) from chamber 131.

The means by which second piston 129 can be controlled to discharge fluid from chamber 131 can vary. In one embodiment, for example, a pump member 133 can be operatively coupled to a second pump inlet 135 on sampling module 104. Inlet 135 is positioned above second piston 129 and by applying positive pressure above second piston 129, pump member 133 can cause second piston 129 to move downward and discharge a sample (or sanitizing fluid) from chamber 131.

If desired, pump member 133 can also provide a negative pressure on second piston 129 to cause it to move upwards. However, because the enclosed container contents are generally under pressure, second piston 129, at least in some cases, will be forced upward by the pressure of the sample (or sanitizing fluid) and additional forces from pump member 133 may not be required to draw the same.

FIGS. 3-11 are schematic representations of the operation of sampling system 100. As described in more detail below, sampling system 100 can be inserted into the enclosed container 102 and can operate to sanitize or sterilize a flow path from the point of insertion with enclosed container 102 through the closed pathway of flow path 106. By being able to sanitize or sterilize the entire path downstream of the insertion point of sampling system 100 into enclosed container 102, the possibility of contaminating the enclosed container 102 and/or the samples captured from the enclosed container 102 is reduced.

Figure 3:
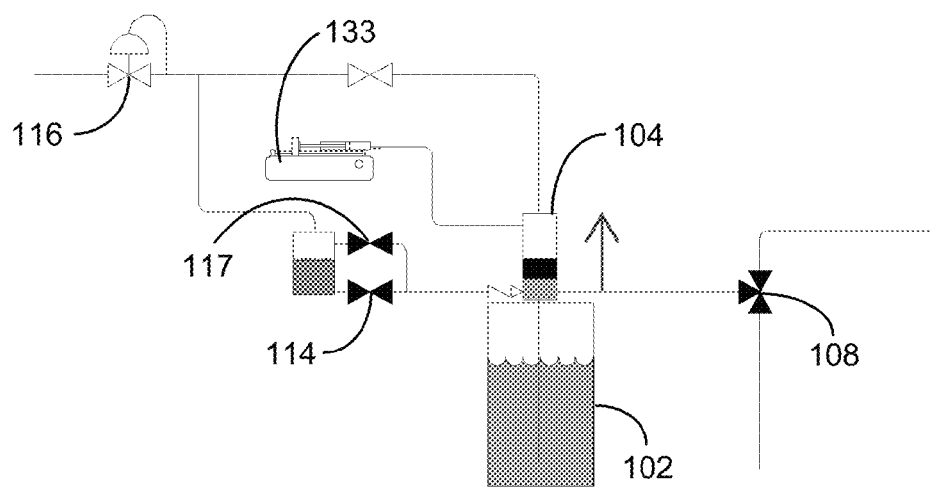
FIG. 3 illustrates a schematic view of a sampling system and its method of operation, including drawing a sample from a container.

FIGS. 3-11 illustrate an exemplary operation of system 100 to draw a sample from an enclosed container 102 in chamber 131 of sampling module 104. As shown in FIG. 3, gas inlet valve 116 can be opened (along with any additional valves between gas inlet valve and sampling module 104) and a negative pressure can be applied at first gas inlet 127 of sampling module 104, creating reduced pressure above first piston 123 and causing first piston 123 to move upward. As first piston 123 moves upwards, sample collection valve 119 moves into the open position, allowing a sample to be drawn in to chamber 131.

Figure 4:
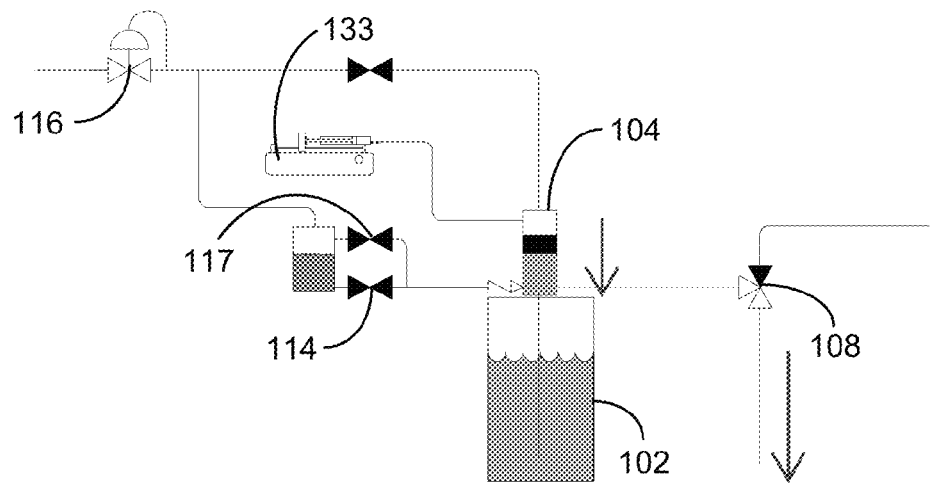
FIG. 4 illustrates a schematic view of a sampling system and its method of operation, including purging a sample from a sampling module.

As shown in FIG. 4, the sample obtained from the enclosed container can be purged to prime chamber 131 to receive another sample. To purge the sample, sample collection valve 119 is closed and pump member 133 causes second piston 129 to move downward to force the sample from chamber 131. Outlet valve 108 can be opened so that the sample can be delivered through flow path 106 to a waste area.

Figure 5:
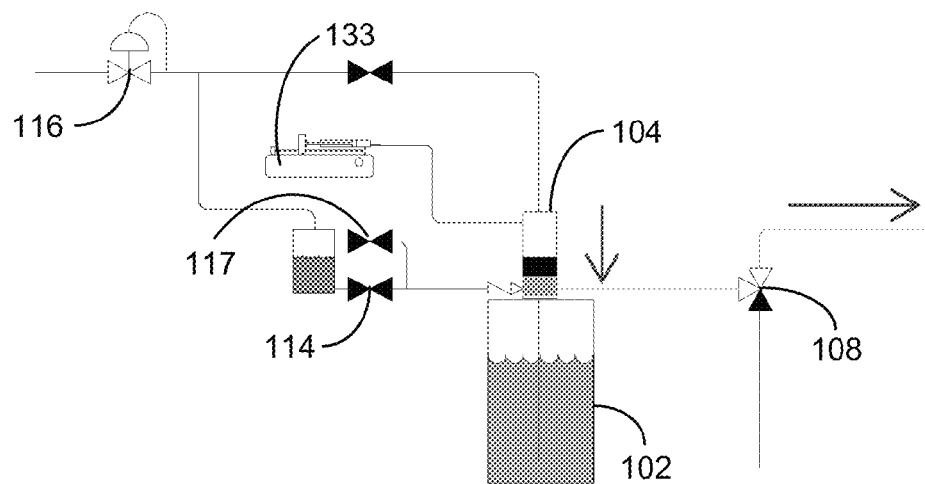
FIG. 5 illustrates a schematic view of a sampling system and its method of operation, delivering a sample from a sampling module.

After the chamber 131 has been primed by the initial sample, another sample can be drawn by the same mechanism noted above in FIG. 3. Once the second sample is drawn, sample collection valve 119 can be closed and pump member 133 causes second piston 128 to again move downward to discharge the second sample from chamber 131 to another location for further analysis. For example, FIG. 5 illustrates outlet valve 108 opened to deliver the second sample to a different location than that shown in FIG. 4. The different location can comprise, for example, a sample/analyzer 110 as shown in FIG. 1.

Figure 6:
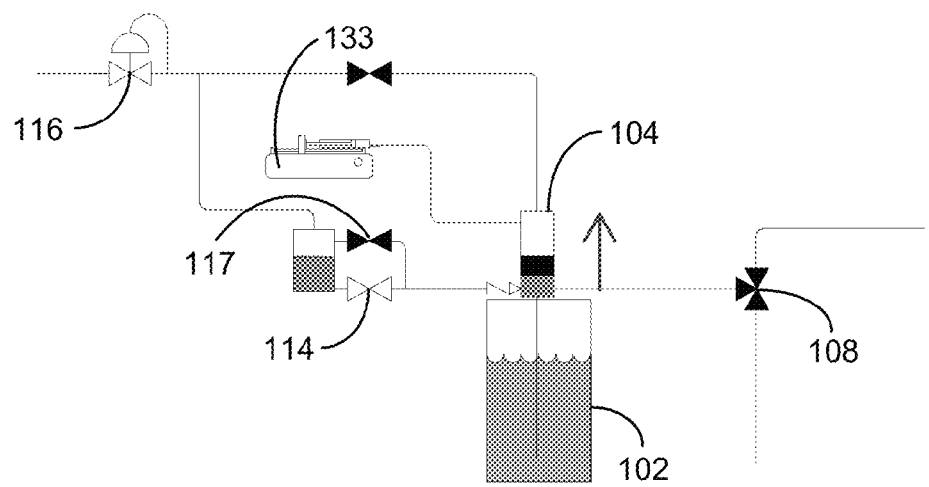
FIG. 6 illustrates a schematic view of a sampling system and its method of operation, including purging a sample from a sampling module.

FIG. 6 illustrates a sanitizing procedure in which a sanitizing fluid is directed into flow path 106 through an open sanitizing fluid inlet valve 114. To flush the system, the sample collection valve is closed and sanitizing fluid is directed along flow path 106, including along the portions of flow path 106 that are in contact with samples that are drawn from the enclosed container 102 and dispensed from flow path 106. For example, sanitizing fluid is directed along flow path 106 past sample collection valve 119 to outlet valve 108. As sanitizing fluid comes into contact with the internal surfaces that define flow path 106, those surfaces are sanitized or sterilized.

Figure 7:
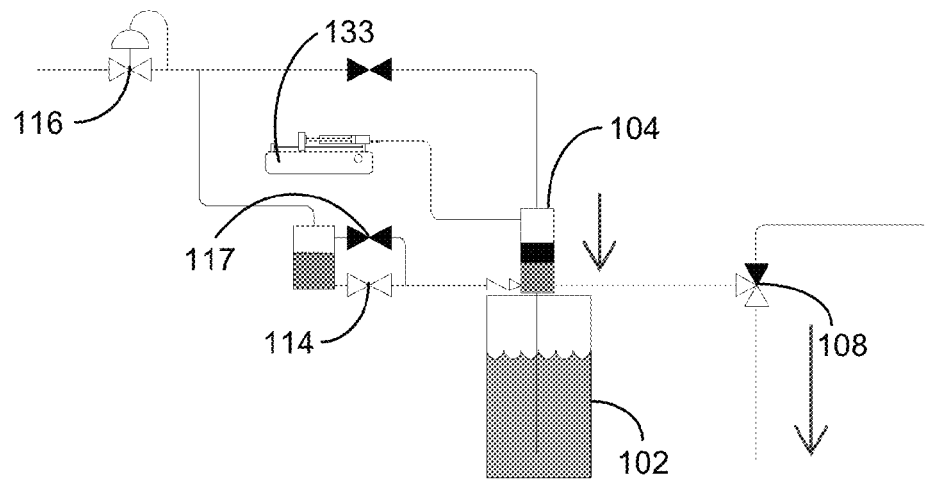
FIG. 7 illustrates a schematic view of a sampling system and its method of operation, including flushing a sampling module.
Figure 8:
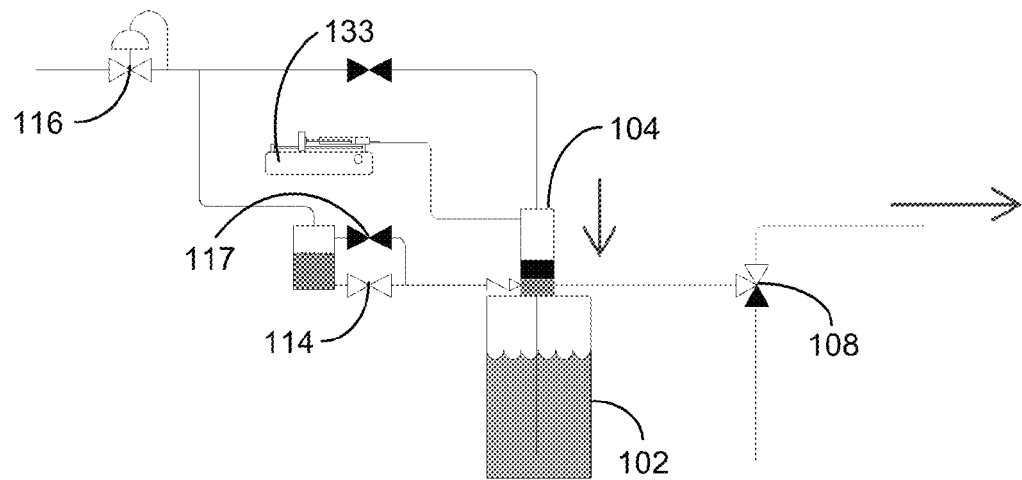
FIG. 8 illustrates a schematic view of a sampling system and its method of operation, including flushing a sampling module.

As shown in FIG. 7, once the sanitizing fluid flushes the fluid flow path, the sample collection valve can remain closed and the outlet valve 108 can be opened to permit sanitizing fluid to be dispensed to a waste area. To further flush the delivery line, sanitizing fluid can also be directed along the path to the sample/analyzer 110 as shown in FIG. 8.

Figure 9:
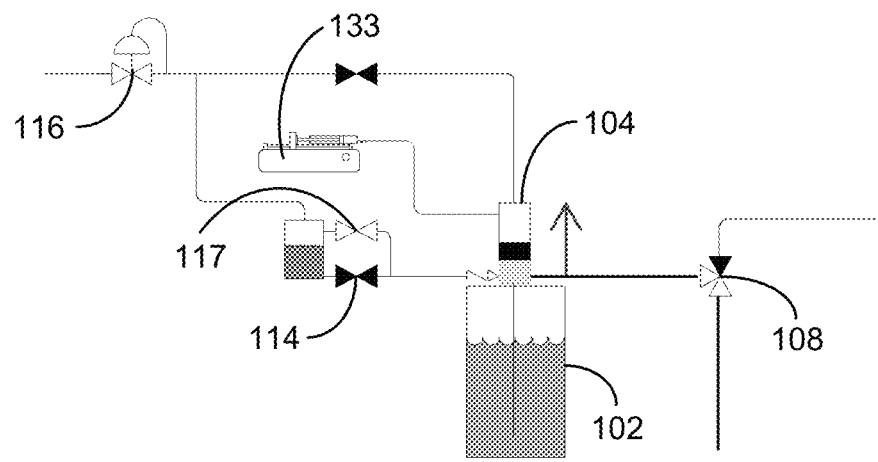
FIG. 9 illustrates a schematic view of a sampling system and its method of operation, including purging sanitizing fluids from a sampling module.
Figure 10:
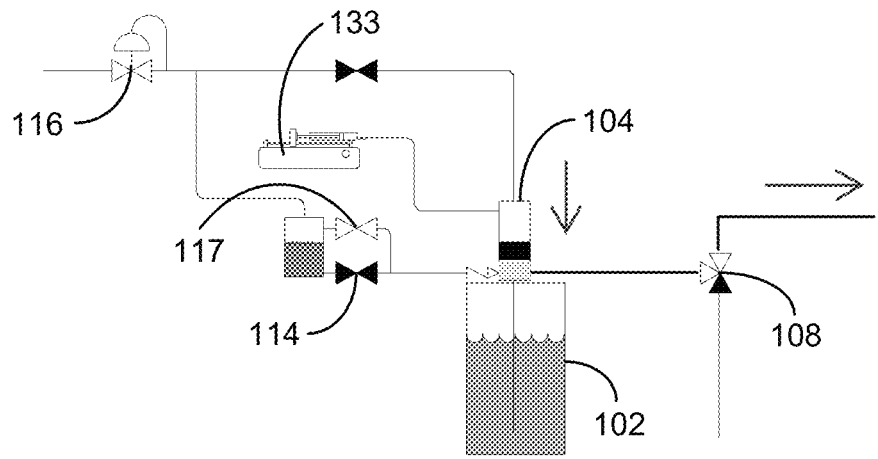
FIG. 10 illustrates a schematic view of a sampling system and its method of operation, including purging gas from a sampling module.

Referring now to FIG. 9, sanitizing fluid inlet valve 114 is closed and first and second gas inlet valves 116, 117 can be opened to allow a gas (e.g., air) to enter flow path 106. As shown in FIG. 9, gas can also be directed along flow path 106, including along the portions of flow path 106 that sanitizing fluid contacted. In this manner, any remaining sanitizing fluid can be purged from flow path 106. If desired, a filter (e.g., a sterile air filter) can be provided upstream of gas inlet valve 116 to ensure that the gas that enters flow path 106 is substantially free of impurities and/or contaminants. FIG. 10 illustrates additional purging of sanitizing fluid along the path to the sample/analyzer 110. As shown in FIGS. 9 and 10, the second piston can be cycled up and down.

Figure 11:
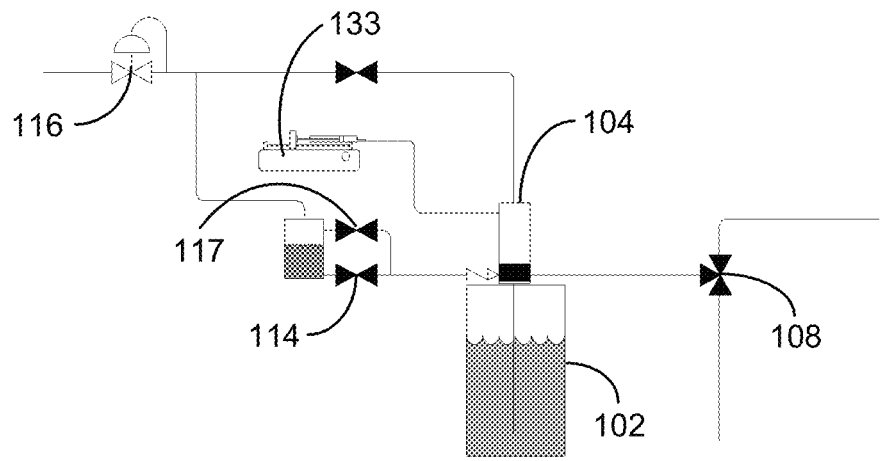
FIG. 11 illustrates a schematic view of a sampling system and its method of operation.

FIG. 11 illustrates the system ready to obtain the next sample with all valves are closed. To start the process over again, a priming sample can be drawn as described above and as shown in FIG. 3.

Figure 12:
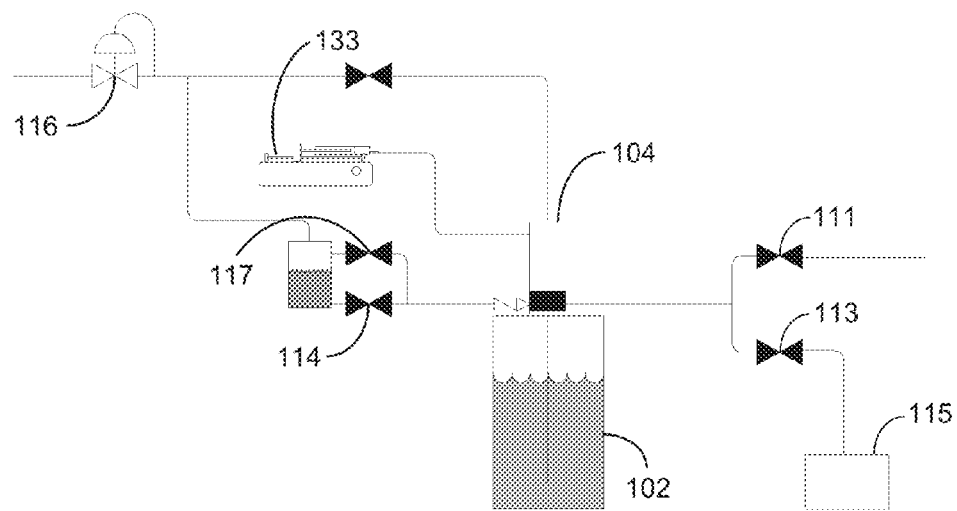
FIG. 12 illustrates a schematic view of a sampling system and its method of operation.

FIG. 12 illustrates another exemplary embodiment of a sampling system. The sampling system depicted in FIG. 12 is similar to that shown in FIGS. 3-11, except two outlet valves 111, 113 are positioned downstream of sampling module 104. At least one of the outlet valves (e.g., 113) can open to allow delivery of samples or waste to a vessel 115. In this embodiment, the sample can be delivered to vessel 115 from which all or a portion of the sample can be drawn into an analyzer. Waste can be discharged through outlet valve 111. Alternatively, waste (e.g., primed sample, sanitizing fluid, purge gas) can be discharged through vessel 115.

The systems disclosed herein can be used with various enclosed containers, including small scale bioreactors where they may be particularly advantageous. For example, in such embodiments, a low dead volume sample pump and concentric actuated foot valve mounted on a dip tube port of a reactor can draw small samples—either manually or automatically—from a bioreactor with little or no dilution of the sample. Thus, in operation, a foot valve can be opened and the piston of the pump can be drawn up a fraction of its capacity to pull a small sample (e.g., <1 ml) into the pump cavity (i.e., chamber). The foot valve can then be closed and the contents of the pump can be pushed to waste to purge the dip tube and prime the pump for the actual sample. The foot valve can be opened a second time and a full sample volume (as specified by operator settings) can be pulled into the pump and the valve can be closed. The sample can then be pumped through valves, as controlled by a controller, to the sample destination. As described herein, the sample delivery can be followed by a flush of a sanitizing solution and air purge to waste.

Using the systems described herein, very small whole broth samples (e.g., 10 ml or less) can be drawn and delivered to desired destination, including destinations that are significantly removed from the bioreactor itself (e.g., 30 feet or more away). In some embodiments, sampling cycle time can be 5 minutes or less. In addition, sample sizes can be readily adjusted by simply adjusting the length of travel of the piston during sample collection.

The automated sampling systems described herein can advantageously allow for more frequent collection of data, reduce sampling variation and human error associated with the capturing of samples, and reduce costs by reducing labor requirements associated with manual sampling.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A sampling system for collecting a fluid sample from an enclosed container, the system comprising:
 (a) a sampling module having a sample collection valve operable between an open position and a closed position, a chamber, and a moveable member within the chamber;
 (b) a first outlet valve operable between an open and closed position;
 (c) a fluid flow path interconnecting the sample collection valve and first outlet valve;
 (d) a sanitizing fluid valve operable to permit sanitizing fluid to be delivered into the fluid flow path; and
 (e) a purge gas valve operable to permit purge gas to be delivered into the fluid flow path;
 wherein the sampling module can withdraw a sample from the enclosed container into the chamber when the sample collection valve is in the open position, and the moveable member can discharge the sample from the chamber and into the fluid flow path of the sampling system for subsequent analysis when the sample collection valve is in the closed position.

2. The system of claim 1, wherein the sampling module comprises a syringe pump and the moveable member comprises a piston member within the chamber of the sampling module.

3. The system of claim 1, further comprising a pump member, the pump member being operatively coupled to the sampling module to cause the moveable member to move within the chamber to discharge fluid from within the chamber.

4. The system of claim 1, wherein the first outlet valve opens to allow the sample to pass through the first outlet valve.

5. The system of claim 4, further comprising a vessel for storing the sample after it passes through the first outlet valve.

6. The system of claim 4, wherein the first outlet valve opens to allow a sanitizing fluid to pass through the first outlet valve for delivery to a waste area.

7. The system of claim 4, further comprising a second outlet valve that opens to allow a sanitizing fluid to pass through the first outlet valve for delivery to a waste area.

8. A sampling system for collecting a fluid sample from an enclosed container, the system comprising:
 (a) a sampling module having a sample collection valve operable between an open position and a closed position, a chamber, and a moveable member within the chamber;
 (b) a first outlet valve operable between a waste delivery position and a non-waste delivery position;
 (c) a fluid flow path interconnecting the sample collection valve and first outlet valve;
 (d) a sanitizing fluid inlet into the fluid flow path; and
 (e) a gas inlet into the fluid flow path;
 wherein the sampling module can withdraw a sample from the enclosed container into the chamber when the sample collection valve is in the open position, and the moveable member can discharge the sample from the chamber and into the fluid flow path of the sampling system for subsequent analysis when the sample collection valve is in the closed position.

9. The sampling system of claim 8, wherein the sanitizing fluid inlet and the gas inlet comprise a single inlet into the fluid flow path.

10. The sampling system of claim 9, further comprising a sanitizing fluid reservoir.

11. The sampling system of claim 8, wherein the sampling module comprises a syringe pump and the moveable member comprises a piston member within the chamber of the sampling module.

12. The sampling system of claim 8, further comprising a pump member, the pump member being operatively coupled to the sampling module to cause the moveable member to move within the chamber to discharge fluid from within the chamber.

13. The sampling system of claim 8, wherein, after discharge of the sample for subsequent analysis and with the first outlet valve in the non-waste delivery position, a sanitizing fluid can be introduced into the fluid flow path via the sanitizing fluid inlet to sanitize the sampling system along the fluid flow path, and
 wherein, after sanitizing the sampling system, the first outlet valve can be moved to the waste delivery position and a gas can be introduced into the fluid flow path and discharged out the first outlet valve.

14. The sampling system of claim 8, wherein the sanitizing fluid inlet is at an upstream portion of the fluid flow path and the first outlet valve is at a downstream portion of the fluid flow path, and a sanitizing fluid can flow through the fluid flow path from between the sanitizing fluid inlet to the first outlet valve to sanitize the fluid flow path therebetween.

15. The sampling system of claim 8, wherein the non-waste delivery position of the first outlet valve comprises a first orientation wherein the sample in the fluid flow path can pass through the first outlet valve for subsequent analysis and a second orientation wherein no fluid can pass through the first outlet valve.

16. The sampling system of claim 8, wherein the sanitizing fluid inlet and gas inlet are both positioned upstream of the sample collection valve.

17. A method of collecting a fluid sample from an enclosed container, the method comprising: positioning a sampling module within a dip tube port of the enclosed container: opening a sample collection valve in the sampling module and drawing a fluid sample from the enclosed container into a chamber of the sampling module: directing the fluid sample out of the chamber along a fluid flow path; discharging the fluid sample out of the fluid flow path for subsequent analysis: closing the sample collection valve: closing a waste valve and directing sanitizing fluid through a sanitizing fluid inlet along the fluid flow path past the closed sample collection valve to sanitize the fluid flow path: and discharging the sanitizing fluid out of the fluid flow path, wherein after discharging the sanitizing fluid but before drawing another fluid sample, the method further includes opening the waste valve and directing a gas through a gas inlet and along the fluid flow path, and discharging the gas through the open waste valve to purge the sanitizing fluid from the fluid flow path, wherein the act of directing the fluid sample out of the chamber along the fluid flow path comprises causing a piston to move towards the fluid sample to force the fluid sample out of the chamber.

* * * * *